United States Patent
Kwak et al.

(10) Patent No.: US 7,388,127 B2
(45) Date of Patent: Jun. 17, 2008

(54) **MULTIPLE STRESS-INDUCIBLE PEROXIDASE PROMOTER DERIVED FROM *IPOMOEA BATATAS***

(75) Inventors: Sang-Soo Kwak, Daejeon (KR); Suk-Yoon Kwon, Daejeon (KR); Haeng-Soon Lee, Daejeon (KR); Sun-Hwa Ryu, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 195 days.

(21) Appl. No.: 10/597,945

(22) PCT Filed: Feb. 24, 2004

(86) PCT No.: PCT/KR2004/000381

§ 371 (c)(1),
(2), (4) Date: Aug. 11, 2006

(87) PCT Pub. No.: WO2005/080557

PCT Pub. Date: Sep. 1, 2005

(65) Prior Publication Data

US 2007/0250963 A1    Oct. 25, 2007

(51) Int. Cl.
*A01H 5/00* (2006.01)
*C12N 15/82* (2006.01)
*C12N 5/14* (2006.01)
*C12N 15/63* (2006.01)
*C07H 21/04* (2006.01)

(52) U.S. Cl. .......... 800/295; 800/278; 536/24.1; 435/320.1; 435/419; 435/468

(58) Field of Classification Search ............ None
See application file for complete search history.

(56) References Cited

U.S. PATENT DOCUMENTS

2003/0186277 A1*  10/2003  Olek et al. ............... 435/6

FOREIGN PATENT DOCUMENTS

KR   2004-0096017 A   11/2004
WO   WO 01/31018 A1   5/2001

OTHER PUBLICATIONS

Park et al., "Differential expression of six novel peroxidase cDNAs from cell cultures of sweetpotato in response to stress," Mol. Gen. Genomics 269: 542-552 (2003).
Kim et al., "A novel oxidative stress-inducible peroxidase promoter from sweetpotato: molecular cloning and characterization in transgenic tobacco plants and cultured cells," Plant Molecular Biology 51: 831-838 (2003).
Curtis et al., "A Peroxidase Gene Promoter Induced by Phytopathogens and Methyl Jasmonate in Transgenic Plants," Molecular Plant-Microbe Interactions 10:3 326-338 (1997).
Kim et al., "Differential expression of four sweet potato peroxidase genes in response to abscisic acid and ethephon," Phytochemistry 54: 19-22 (2000).

* cited by examiner

*Primary Examiner*—Phuong T Bui
*Assistant Examiner*—Vinod Kumar
(74) *Attorney, Agent, or Firm*—JHK Law; Joseph Hyosuk Kim (57) ABSTRACT

The present invention relates to a multiple stress inducible promoter, more particularly to a multiple stress inducible peroxidase promoter derived by *Ipomoea batatas*, a expression vector for production of transgenic plants with enhanced tolerance to multiple stress containing the promoter, a transgenic plant cell and plants transduced by the expression vector, and a method for generating the transgenic plants. Promoter of present invention will be biotechnologically useful for development of industrial transgenic plants with enhanced toleransce to multiple stress and plant cell lines to produce useful proteins.

10 Claims, 3 Drawing Sheets

FIG. 1a

```
-2433                                              CCTCATGGAGTATTCTCATAACTCTCTTCAGTA
-2400  TGAATGAATCATACAATACAACGCAGCGACGAATAGACTTCGCCCTGAACTAGACATACGACAACATAGCCACCATACGG
-2320  GAAACGCACTTCAAGCTCTTTATCCCGTAGGCTGCAACACCATAACGACATAACGACCACTGGGCAAGGGCATTTACAGC
-2240  CACCCGTGGGTCAATCAAGGTCCTCCTGACTCACTTTAGAAACTAAGGGTTTGAAAACATGATCTTTCCTTCAGTTTTTC
-2160  TTACAACAAATCATTCACTTTGGAGACATTTCACAATTGAGTCCAATACTTAAACCGGCTACTTCATTAGCCCCTGAAGG
-2080  ATTTTAAAAAAAAGTTTCACTGCCCGCGAGGCTCTTCAAACATCTTTTCCTCATTATCAAGTGAGGCATTTTTCCTCAAAAG
-2000  TAAGGTTTTGAGAACCTTTATATCAAATAGCATACGTTTTTCAACGTAAGTTTCATAACATTTACTTGCCATCTCACCA
-1920  CTTCGTCTTAAACAATCTAGGATATTCTTAGATATTCTTCATACTCAAGTCTCAGCACTTGAAATCAATCAAGACTCTTAC
-1840  ACTAACAATTCCTCAATATACCTCATAATATCATCTCTACTTAAACTAGAGAGATTTCCAACTCTCAATTAATCACCAAA
-1760  GGTAACTCTCCAAATATCCAAATGGAAGGTTTCAACTTCCAAACTAATACCAAACCAACCGGACTAATCATAATCATATT
-1680  CATAATCATAAATTGTTTCTAACTGCCGCTGTCCAGAAATTACAGTTTTGCGCAGTCCGAAAGATTGAGCCGGTAACAAT
-1600  AGTTCCCGAACTCTTTTTCACTTGAAATTTTTATGGTAGAACCCTAACTTATAGTACTTGATATCCATAAAAGTTTTGG
-1520  TCACCTAGGTTCACGAATTAACACAGAAAATTACATCTTTGCCCTTGGCAGTGGGCTGTCCGGAATTCTGTCTCTCTGGA
-1440  CCAGTTTTGGCAAACAATTTTTGAAACCACACTTATACTACTCCAAAAATTATGAAATTTTTATGGTAGCTTCTACACTTA
-1360  TAGAACTACATGTATAAAAAATATTGGGTCAAATACCTTACCGATTTTTCCCAAATATTCACGGAACTTACTGCCAGAA
-1280  TCTACGCTGCTTTTTCCTTTCACTATTTTCACAACTATAAGCATATATGGGCATAAAATATGACATGAACATGCATGAACC
-1200  AATGCAGGGTGAAAGTAAGATTGAATATACTGATACTACAATTAACTAATGATAAAGTATAACTTTTGTAAAAAATTTGA
-1120  TTTTTTTTTTTGAATGAATTCATATACTCCAAGATTTTCCTCATTTAATTAAATTTCTATCCTCATGTTGAACCCATTAA
-1040  TCGAATAATTGACATATTAGATAAACTTAGCCATCATATGACATTTGATCATGATTCATGATTTTTAAAAAATAAAACA
-960   AAATTATGAAAGGGTAATGAAATATTTTAAAAAAATTATGTAAACCCTGTAATCTAGTAATCTGTACAATAATAATTTTG
-880   TTTCAACTAAGACGATGTTGCCAAAAGTATAATTAAACTTGTGATCTTCGTACAATAATTATGCTTCACGCACTCAACTA
-800   GTCACATCTTTCCAGGCAAAATTTACTTTTCTATGAATATGAGAAGTTCCATCTATGGAAATAACGGATTATTTATCTAA
-720   TTTTCAAATTCTATATATATAGTCTCGAGTGGAACAAAAATAGAACTAATTTGAACAAATCAAAGTCTAAGAAAATAATA
-640   CATGCTTTAGCAGCAAAAATAAGAATGGTACTATACTTAATCGTCATCATAGTCTTCAACCCTGCATATAGCACACTTAA
-560   CATTTTATATTCAAATATACTTTAATTTAGTCATGATAATACAACTCACCTACTCCATTATAGCCGATAATACAACTCAC
-480   CTAGCTACTCCATTATAGTCCAACAATATCAAATGAATAAAATAGTAATGGTGACTTAAAGGGCTGAATCCAACATATAT
-400   TCTGACATTTAAAAATGCTAACGTACCGTTAGATTAGTATAATGAAATAAAGTTAATCATTCTCTATATTTGATGATGGT
-320   AATTAGTATCATGGTAAGGTGTTTTATCGTGGCAGCATGAGTGCATGACAAACGCATATATTATTATTAAAACAAAATAG
-240   TACTCCAATCATAATAAATTATCTTATATTATATTGCCAACAATTAAAAATTCAAATTAGAACAAATTAAATCTCAGTTT
-160   GCTTTATTATATTATTATCAACAATAATAATTTAATACTGATCGAAGAACTTTCCCTTTCAAGTTCTCTATTTAAGGAAG
-80    CCTGAGAAGCCATTAATCCTCATCATCAGCTCGACCACTCATTTCTTCTTCATACTTCCTTTGCTGTGATAATCATCATC
```

FIG. 1b

```
ATGGCTTCCTTTGTCACTCGGCTCAGCCTGGCCCTTAGCTTCATCGCCCTAGCCCTAGCTGGCTTCTCCATTTACCAGAA    80
 M  A  S  F  V  T  R  L  S  L  A  L  S  F  I  A  L  A  L  A  G  F  S  I  Y  Q  N

TACCCATACAGCCATGAAAGGGCAGCTTAAGCTCACCCCAAAGTGGCTGCTAGACAACACTCTAGAGTGGTCAGTGGCCG   160
  T  H  T  A  M  K  G  Q  L  K  L  T  P  K  W  L  L  D  N  T  L  E  S  S  V  A

ACGTGCTCTCACTACGGCTAGGCATCTCCTCCGGCAAGCTTTCCGACGAAGACTGCATATTCTCCGCCGTTAAGGAAGTG   240
 D  V  L  S  L  R  L  G  I  S  S  G  K  L  S  D  E  D  C  I  F  S  A  V  K  E  V

GTGGACGCCGCCATTGATGCAGAAACCCGCATGGGTGCTTCCCTCATTCGGCTCTTCTTCCATGACTGCTTTGTTGATGT   320
  V  D  A  A  I  D  A  E  T  R  M  G  A  S  L  I  R  L  F  F  H  D  C  F  V  D

ACGTACGCTAATTTTGTACGATGATGTTTTTTTTTTTTTTTTTTTTTTTCCCACTGCATTATATTAGGAAATTAAACAGA   400

TTGAAATGTGTGTGTTATTAATGTATTATCTGCAGGGTTGTGACGCAGGTCTTCTACTAAACGATACAACCTACTTTCACCCCG   480
                                G  C  D  A  G  L  L  L  N  D  T  P  T  F  T  G

AGAACAGACCGCCGGCGGCAATAATAACTCAGTCAGACGGTTTTGAGGGTGATACAACAAGCTAAAGAGAATGTGATAACCA   560
 E  Q  T  A  G  G  N  N  N  S  V  T  G  F  E  V  I  Q  Q  A  K  E  N  V  I  T  K

AATGTCCCTACATACAAGTATCTTGTGCCCGACATCTTATCCATTGCTGCCCGTGATTCTTTCCAGAGAGTAAGTCCATTT   640
  C  P  Y  I  Q  V  S  G  A  D  I  L  S  I  A  A  R  D  S  F  Q  R

ATTTCTAAACGGTTGAAATTAATAAGAACAAGAATCCAAACAAATAACAGACAGTAAAAAAAAAAGATTTATGTGGTTTGA   720

CAATATGTTGAAATTGTTTTTTATATTTAATGACTAGTATTTATGCATTATATTTATATGCAACTCTAAACATGCAGTTTA   800
                                                                               F

CTGGAGAAACGTACACCGTGACTCTGGGAAGACTCGATGCAAGAACGGCGAACCTTACCGGAGCTAACACCCAACTCGTC   880
 L  G  E  T  Y  T  V  T  L  G  R  L  D  A  R  T  A  N  L  T  G  A  N  T  Q  L  V

GGACCAAACGAGGAATTGGCATCGCAAGTCGAGAAATTTGCCGCCGAAAGGGTTCTCCGAAACGGAGCTAGTGGCCTTGTT   960
  G  P  N  E  E  L  A  S  Q  V  E  K  F  A  A  K  G  F  S  E  T  E  L  V  A  L  L

AGGTGTTCACACCGGTTGGGTTTTCGAGATGTCCGGCTTTTATGCCGTTCCCATTTTCATCAATCCCGCCCGGGCCTCGACGC  1040
 G  V  H  T  V  G  F  S  R  C  P  L  L  C  V  P  I  F  I  N  P  A  R  A  S  T

TGCAATGCAACTGTCCGGTGAGTCCCGACGGACACCGGCCTGGTGGGCCTGGACCCCACTCCGTTGACGTGGGACCAAAGT  1120
 L  Q  C  N  C  P  V  S  P  D  T  G  L  V  G  L  D  P  T  P  L  T  W  D  Q  S

TTTTACTCCGACGTGGCTAACGGACAAGGGCTTCTGTTCTCCGACAACGAGCTGATGAATAGCAACACCACCAGCGCCGCC  1200
 F  Y  S  D  V  A  N  G  Q  G  L  L  F  S  D  N  E  L  M  N  S  N  T  T  S  A  A

CGTTAGGAGGTACAGGGACGAGATGGACGCTTTTCTCGCCGATTTCGCCGCCGCCATGGTGAAGATGAGCCTCCTGCCCGC  1280
  V  R  R  Y  R  D  E  M  D  A  F  L  A  D  F  A  A  A  M  V  K  M  S  L  L  P

CGTCCCCGGGAGTGGAGCTGGAAATCCGAGAGGTTTGCAGCGAGGTGAATGCAACACAGTTGCATCCATGTGAAGTTCG   1360
 P  S  P  G  V  E  L  E  I  R  E  V  C  S  E  V  N  A  N  T  V  A  S  M

TTCCCATGGACATCAATAACGTCTGTGATTCTGTGAAAGTTTTACTGGGACTGTGAAGAATTTTCACTTTCTGTTGTTTC   1440

TGAAATAAAAAAGATTTTTTTTTTTATGTCCTAACAAAACTTGTATTACTGAATAAAATTTATAAATTTGTTA         1512
```

(SEQ ID NO:1)

MULTIPLE STRESS-INDUCIBLE PEROXIDASE PROMOTER DERIVED FROM IPOMOEA BATATAS

FIELD OF THE INVENTION

The present invention relates to a multiple stress inducible promoter, more particularly to a multiple stress inducible peroxidase promoter derived from a sweetpotato (*Ipomoea batatas*), an expression vector for production of transgenic plants with enhanced tolerance to multiple stress containing the promoter, a transgenic plant cell line and plants transfected by the expression vector, and a method for generating the transgenic plants.

BACKGROUND

When plants get stress including environmental or biological stress from pathogenic bacteria, noxious insects, or viruses, oxygen inside which is an essential ingredient for a life changes into reactive oxygen species (ROS) such as superoxide anion radical ($O_2^-$), hydrogen peroxide ($H_2O_2$), hydroxyl radical, etc, causing serious disorders. In order to eliminate such active oxygen, a living body has macromolecular anti-oxidant enzymes such as superoxide dismutase (SOD: EC 1.15.1.1), peroxidase (POD) and catalase (CAT), and low molecular weight anti-oxidant substances such as vitamin C, vitamin E, glutathion, etc.

Peroxidase is an enzyme reducing hydrogen peroxide in the presence of electron donors, and is largely found in plant cells. Owing to its high sensitivity to enzyme reaction, peroxidase has been used as a reagent for many clinical tests. In addition to the importance in industry, peroxidase also draws an attention of scientists since it plays an important role in plant reaction against stress from outside. In general, the activity of plant peroxidase increases by various environmental stresses. In particular, plant culture cells show high activity of peroxidase because the cells are cultured under huge oxidative stress. According to an earlier report, peroxidase is mass-produced in sweetpotato culture cells more than in any other plant culture cells (*Phytochemistry*, 39, 981-984, 1995).

As of today, genes coding peroxidase included in some particular plants have been found in about 20 different plant species such as horseradish, barley, wheat, rape, *Arabidopsis thaliana*, tobacco, spinach, rice plant, etc. Recently, a total base sequence of *Araidopsis* has been identified, from which 73 peroxidase genes have been confirmed (*Gene*, 288, 129-138, 2002). But, the function of each individual peroxidase has not been explained yet. Peroxidase genes of a sweetpotato have been first reported by the present inventors. Particularly, the present inventors have separated three acidic peroxidase genes (swpa1, swpa2, swpa3) and a neutral peroxidase gene (swpn1) from sweetpotato culture cells, and have reported that those genes are expressed specifically in sweetpotato culture cells and found multiply in genome, and have further confirmed that peroxidase can be mass-produced stably by transfecting cells or plants with either some parts or a whole peroxidase gene (*Mol. Gen. Genet.*, 255, 382-391, 1997; *Mol. Genet. Genet.*, 261, 941-947, 1999).

In pervious studies, the present inventors separated novel acidic peroxidase genes 'swpa4, 'swpa5, and 'swpa6' along with basic peroxidase genes 'swpb1', 'swpb2' and 'swpb3' whose base sequences were all disclosed (Korea Patent Application #2003-28811; *Mol. Genet. Genomics*, 261, 941-947, 2003). Swpa4 was expressed strongly in sweetpotato culture cells but was not expressed in normal plant tissues. Swpa4 was highly expressed not only by biological stress like pathogenic bacteria (Pectobacterium chrysanhemi, KCTC 2569) but also by non-biological stresses such as wounding, methyl viologen and hydrogen peroxide having a herbicial activity by generating active oxygen, NaCl, methyl jasmonate, abscisic acd, low temperature of 15° C. and high temperature of 37° C., etc.

Thus, the present inventors have separated genomic DNA from a sweetpotato which is coding peroxidase expressed actively not only by biological stress but also by many other physical or chemical stresses, and completed this invention by confirming that a promoter of the same is valuable enough in industry.

SUMMARY OF THE INVENTION

It is an object of this invention to provide a multiple stress-resistant promoter sequence including a base sequence represented by SEQ. ID. No 2.

It is also an object of this invention to provide an expression vector for the production of a multiple stress-resistant transformant including the above promoter sequence, target substance coding sequence and transcription terminator sequence.

It is a further object of this invention to provide multiple stress-resistant transgenic cells prepared by transfecting host plant cells with the above expression vector.

It is also an object of this invention to provide a multiple stress-resistant transgenic plant prepared by transfecting a host plant with the above expression vector using an *Agrobacterium*.

It is also an object of this invention to provide a preparation method for the above multiple stress-resistant transgenic plant.

DETAILED DESCRIPTION OF PREFERRED EMBODIMENTS

In order to achieve the above object, the present invention provides a multiple stress-resistant promoter sequence including a base sequence represented by SEQ. ID. No 2.

The present invention also provides an expression vector for the production of a multiple stress-resistant transformant including the above promoter sequence, target substance coding sequence and transcription terminator sequence.

The present invention further provides multiple stress-resistant transgenic cells prepared by transfecting host plant cells with the above expression vector.

The present invention also provides a multiple-stress-resistant transgenic plant prepared by transfecting a host plant with the above expression vector using an *Agrobacterium*.

The present invention also provides a preparation method for the above multiple stress-resistant transgenic plant.

"SWPA4 promoter" is a base sequence located on -1~-2433 region of a promoter sequence having a base sequence represented by SEQ. ID. No 11, and induces transcription of a related gene under a required condition.

"Active fragment of SWPA4 promoter" is a base sequence containing some of base sequence located on -1~-2433 region of swpa4 genomic gene sequence represented by SEQ. ID. No 1, and endows a gene properly linked with a SWPA4 promoter activity.

"Transformant" means a plant culture cell line or a plant transfected with DNA construct composed of SWPA4 promoter and properly linked DNA sequence coding relevant substances.

"Multiple stress" includes biological or non-biological stress, for example, wound, active oxygen species, heat, moisture, temperature, salt, air pollution, UV, heavy metals, chemical herbicides, pathogenic bacteria, etc.

Hereinafter, the present invention is described in detail.

The present invention provides a multiple stress-resistant promoter sequence including a base sequence represented by SEQ. ID. No 2.

The promoter sequence of the present invention is preferably selected from a group consisting of base sequences represented by SEQ ID NOS:2-11. The promoter sequence represented by SEQ. ID. No 11 is a whole promoter sequence located in front of transcription beginning region (ATG) included in peroxidase SWPA4 genomic gene derived from a sweetpotato which is represented by SEQ. ID. No 1. SEQ. ID. No 2, SEQ. ID. No 3, SEQ. ID. No 4, SEQ. ID. No 5, SEQ. ID. No 6, SEQ. ID. No 7, SEQ. ID. No 8, SEQ. ID. No 9 and SEQ. ID. No 10 are all fragment sequences located on the —110th, -177th, -306th, -366th, -433rd, -818th, -1199th, -1467th and 1934th sites each from the end of a whole SWPA4 promoter sequence (located just in front of transcription beginning region).

A full-length SWPA4 promoter having a base sequence represented by SEQ. ID. No 11 includes specific regions for regulatory elements of various eukaryotic promoters, and TATA box (TATTTAA) for transcription beginning locates on $-92^{nd} \sim -86^{th}$ site. RSTGACTMANA, a consensus sequence of AP-1 which is known as an attachment site for a transcription regulating protein and a major element reacting against active oxygen species, locates on between $-431^{st}$ and $-421^{st}$ (Lucibello, FC. et al., *Oncogene*, 8, 1667-1672, 1993). A consensus sequence of ELRE, TTGACC (Rushton, PJ. et al., *EMBO J*, 15, 5690-5700, 1996), whose expression is strongly induced by elicitor generated by a defense mechanism of plant against pathogenic bacteria infection or wound, locates on regions between -2227 and -2232 and between -1329 and -1334 as an inverted repeat sequence. TAACGTA, a consensus sequence of GARE whose expression is regulated by a plant hormone 'gibberellin' (GA), locates on the region between -382 and -376 (Sutoh, K. et al., *Plant J*, 34, 636-645, 2003). AWT-TCAAA, a consensus sequence of ERE whose expression is regulated by a plant hormone 'ethylene' which is related to ripening and aging of a fruit, locates on the region between -192 and -185 (Itzhaki, H. et al., *Proc Natl Acad Sci USA*, 91, 8925-8929, 1994). W-box, on which WRKY protein which plays an important role in resistance against a disease after being expressed by salicylic acid (SA) is attached, locates on the regions between -1993~-1989, and between -1032~-1028 with repeat of TTGAC and also between -2227~-2231 and between -1329~-1333 as an inverted repeat sequence this time (Yu, D. et al., *Plant Cell*, 13, 1527-1540, 2001) AGAAN, a consensus sequence which is a heat shock element (HSE), locates on the promoter region between -182 and -178 (Fernandes, M. et al., *Nucleic Acids Res*, 22, 167-173, 1994) (see FIG. 1a).

In the preferred embodiment of the invention, the present inventors prepared promoter sequences represented by SEQ. ID NOS:2-11 from peroxidase SWPA4 genomic gene represented by SEQ. ID. No 1 included in a sweetpotato, and an expression vector containing the same. Transgenic tobacco cells including various size promoters were also produced by transfecting tobacco culture cells with the expression vector prepared above. An activity of the promoter was investigated by using protoplasts of tobacco cells. As a result, deleted promoter fragments having different sizes, which were represented by SEQ ID NOS:2-11, showed similar activity to or over 4.5-fold (but less than 8.5-fold) higher promoter activity than CaMV35S promoter of a control group (see FIGS. 3a and 3b). A transgenic tobacco plant was produced by inserting an expression vector containing various size deleted promoter fragments into a tobacco leaf section using *Agrobacterium*. Then, stress was induced therein. Promoter activity was investigated after inducing stress. As a result, the activity of GUS (a target gene included in an expression vector) was increased after the treatment of pathogenic bacteria, methyl viologen or causing wound, at least twice as much as before the treatment (see Table 1). Therefore, promoter sequences of the present invention represented by SEQ. ID NOS:2-11 were proved to have higher promoter activity than any conventional promoters, and the activity was strongly enhanced by stress. So, promoter sequences of the present invention can be effectively used for the development of an environmental stress-resistant plant and the production of valuable substances by taking an advantage of the transgenic plant cells obtained thereby.

The present invention also provides an expression vector for the production of a multiple stress-resistant transformant including the above promoter sequence, target substance coding sequence and transcription terminator sequence.

The promoter sequence included in the expression vector of the present invention is preferably selected from base sequences represented by SEQ. ID NOS:2-11.

It is also preferred for a target substance of the invention to include various proteins or peptides having pharmaceutical effects or any other substance giving resistance against stress to a transformant. In the preferred embodiment of the present invention, expression vectors having deletion promoters in various sizes were constructed by cloning each sequence of the promoter represented by SEQ. ID. NOS:2-11 into plasmid vector pBI1221 (CaMV35S promoter, GUS coding sequence and NOS transcription terminator sequence were included) provided by Clontech, Co. Each expression vector prepared above was named, according to the length of a promoter sequence, 'p2433', 'p1934', 'p1467','p1199', 'p818', 'p433', 'p366', 'p306', 'p177'and 'p110'. GUS was used as a target gene for the expression vector of the invention. But, GUS could be replaced by any other target valuable substance coding sequence to construct an expression vector producing a target valuable substance keeping resistance against stress.

The present invention further provides multiple stress-resistant transgenic cells prepared by transfecting host plant cells with the above expression vector and a multiple stress-resistant transgenic plant prepared by transfecting a host plant with the above expression vector using an *Agrobacterium*.

For the preparation of transgenic cells and a transgenic plant of the present invention, the expression vector preferably contained a promoter sequence selected from a group consisting of sequences represented by SEQ ID NOS:2-11. For producing transgenic cells of the present invention, a host cell was preferably selected from a group consisting of tobacco, major agricultural crops such as rice, sweetpotato, etc., and medicinal plants including ginseng. For producing a transgenic plant of the present invention, a host plant was preferably selected from a group consisting of tobacco, major crops such as rice, sweetpotato, etc., and medicinal plants including ginseng.

In the preferred embodiment of the present invention, cells of a tobacco, *Nicotiana tabacum*, were transfected with expression vectors p110, p177, p306, p366, p433, p818, p1199, p1467, p1934 and p2433, each including a promoter sequence selected from a group consisting of sequences represented by SEQ. ID NOS:2-11, using an *Agrobacterium*, resulting in the preparation of transgenic tobacco cells expressing the above expression vectors respectively. Among those transgenic cells, the one cell line that was transfected with expression vector p1467 showed the highest promoter activity, so that it was named 'p1467 (*Nicotiana tabacum* cv.*Xanthi*) cell line' and deposited at KCTC (Korean Collection for Type Culture) of KRIBB (Korea Research Institute of Bioscience and Biotechnology) on February 10, 2004 (Accession No: KCTC 10594BP).

The present invention also provides a preparation method of a multiple stress-resistant transgenic plant comprising the following steps:

1) Constructing an expression vector containing each of a promoter sequence selected from a group consisting of base sequences represented by SEQ ID NOS:2-11, a target valuable substance coding sequence and a transcription terminator sequence; and 2) Transfecting a host plant with the expression vector of the above step 1) using an *Agrobacterium*.

BRIEF DESCRIPTION OF THE DRAWINGS

The application of the preferred embodiments of the present invention is best understood with reference to the accompanying drawings, wherein:

FIG. 1a and FIG. 1b (continuation of FIG. 1a) show a base sequence of genomic gene SWPA4 coding peroxidase of the present invention originated from a sweetpotato and an amino acid sequence translated from the same. The part of base sequence marked with (-) is a promoter sequence (FIG. 1a), the parts marked with base sequence and amino acid sequence together are exons and the parts marked with only base sequence are introns (FIG. 1b).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Separation of Sweetpotato-Originated Peroxidase Genomic DNA SWPA4 and Analysis on Base Sequence of the Same Genomic DNA of sweetpotato-originated peroxidase gene SWPA4 was separated by using GenomWalker kit (Clontech) following the manufacturer's instruction. 2.5 μg of a sweetpotato genomic DNA, extracted by the general method, was digested with restriction enzymes EcoRV, DraI, PvuII, SspI, etc. The digested genomic DNA was purified using phenol/chloroform/ethanol. GenomWalker library was constructed by linking the purified genomic DNA and an adaptor supplied by the kit by using ligase. Based on the library, SWPA4 genomic DNA was obtained by PCR. PCR was performed with GSP1 primer represented by SEQ. ID. No 12, which was established based on the information on 5'-end base sequence of SWPA4 cDNA, and an adaptor primer AP1 represented by SEQ. ID. No 13, which was supplied by the kit above, by using the above genomic DNA as a template. PCR reaction was induced at 94° C. for 25 seconds and at 72° C. for 4 minutes, which was repeated 7 times, and further at 94° C. for 25 seconds and 67° C. for 4 minutes, which was repeated 32 times. After PCR, electrophoresis was performed to confirm some of the products. After diluting the primary PCR product by 50 times, PCR was performed again with GSP2 primer represented by SEQ. ID. No 14, which was prepared on the basis of the information on the base sequence of 5'-end of a sweetpotato originated peroxidase SWPA4 cDNA (Korea Patent Application #2003-28811), and an adaptor primer AP2 represented by SEQ. ID. No 15, which was supplied by the kit. The PCR condition was as follow; at 94° C. for 25 seconds and at 72° C. for 4 minutes (5 cycles), at 94° C. for 25 seconds and 67° C. for 4 minutes (22 cycles). Then, electrophoresis was performed to confirm PCR product. The PCR product was cloned into pGEM-T Easy vector (Promega) and base sequence was investigated. Exon region of SWPA4 gene was amplified by using a primer represented by SEQ. ID. No 16 and an adaptor primer AP1 represented by SEQ. ID. No 13, likewise, intron region of SWPA4 gene was amplified by using a primer represented by SEQ. ID. No 17 and an adaptor primer AP2 represented by SEQ. ID. No 15.

Figure 2:
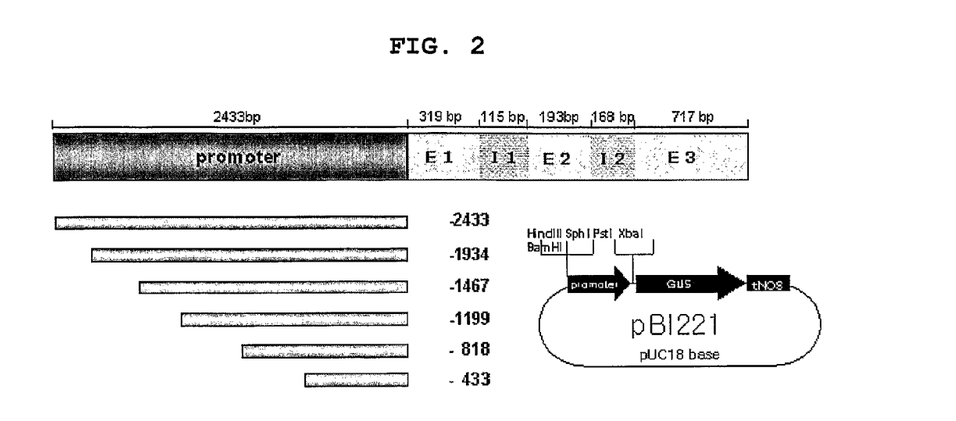
FIG. 2 is a schematic diagram showing the structures of genomic gene SWPA4 coding peroxidase of the present invention and an expression vector for the production of deletion mutants that include deletion promoters. E1, E2 and E3 are exons, and I1 and I2 are introns.

The amplified PCR product was cloned into pGEM-T Easy vector following the same method above, and a base sequence was determined, so that sequence of the genomic gene represented by SEQ. ID. No 1 was obtained (FIGS. 1a and 1b), and named 'SWPA4'. SWPA4 separated from a sweetpotato genome was 3945 bp in total length and composed of three exons, two introns and a 2433 bp long promoter. Base sequence of exon of the genomic gene was confirmed to be identical with that of SWPA4 cDNA (Korea Patent Application #2003-28811), and 5' of each intron began with GT and 3' of them ended with AG, suggesting that it was keeping the rule of GT-AG (FIGS. 1a, 1b and FIG. 2).

Example 2

Investigation of a Promoter Activity of Peroxidase Genomic DNA SWPA4

A promoter of wild type SWPA4 was composed of base sequence represented by SEQ. ID. No 11, ranging from upstream of translation starting point of peroxidase SWPA4 genomic DNA to -2433 bp point (FIGS. 1a and 1b). The characteristics of the base sequence of SWPA4 promoter was investigated by using PLACE and Transfac provided by Computational Biology & Informatics Laboratory.

As a result, SWPA4 promoter was confirmed to have regulatory elements of various eukaryotic promoters, and TATA-box for the translation starting was located between -92 ~-86 (Zhu, Q. et al., Plant Cell, 14, 795-803, 2002). RSTGACT-MANA (SEQ ID NO:31) (Lucibello, FC. et al., Oncogene, 8, 1667-1672, 1993), a consensus sequence of AP1, which has been known as a relevant factor responding to active oxygens and a transcription regulatory protein is attached to, was located between -431~-421. TTGACC (Rushton, PJ. et al., EMBO J, 15, 5690-5700, 1996), a consensus sequence of ELRE which strongly induces a gene expression by elicitor generated by a defense mechanism against germ infection or wound in plants, was found between -2227~-2232, and between -1329~-1334 as an inverted repeat sequence. TAACGTA (Sutoh, K. et al., Plant J, 34, 636-645, 2003), a consensus sequence of GARE whose expression is regulated by gibberellin (GA), a plant hormone in a plant, was located between -382 ~-376. AWTTCAAA (Itzhaki, H. et al., Proc Natl Acad Sci USA, 91, 8925-8929, 1994), a consensus sequence of ERE whose expression is regulated by ethylene, a plant hormone related to ripening and aging of a fruit of a plant, was located between -192 ~-185. W-box (Yu, D. et al., Plant Cell, 13, 1527-1540, 2001), to which WRKY protein expressed by salicylic acid playing an important role in resistance against diseases is attached, was located as a repeat sequence of TTGAC at two regions between -1993 and -1989 and between -1032 and -1028, and located as an inverted repeat sequence at two other regions between -2227 and -2231 and between -1329 and -1333. AGAAN (Femandes, M. et al., Nucleic Acids Res, 22, 167-173, 1994), a consensus sequence of HSE (heat shock element) responding to heat shock was located between -182 and -178 of the promoter (FIG. 1a).

As explained hereinbefore, SWPA4 promoter of the present invention includes many important factors recognizing various types of stress including ROS, so that it can be effectively used for the development of a stress-resistant plant standing against environmental stress.

Example 3

Preparation of Deletion Mutants of SWPA4 Promoter

<3-1> Preparation of Deletion Mutants of 2433 bp~433 bp Long Promoters

In order to prepare deletion mutants of SWPA4 promoter of the present invention, SWPA4 promoter region was amplified by PCR using ExTaq polymerase (Takara) and sequence specific primers. At that time, primers represented by SEQ. ID. No 18 and No 24 were used to amplify a 2433 bp long promoter, primers represented by SEQ. ID. No 19 and No 24 were used to amplify a 1934 bp long promoter, primers represented by SEQ. ID. No 20 and No 24 were used to amplify a 1467 bp long promoter, primers represented by SEQ. ID. No 21 and No 24 were used to amplify a 1199 bp long promoter, primers represented by SEQ. ID. No 22 and No 24 were used to amplify a 818 bp long promoter, and primers represented by SEQ. ID. No 23 and No 24 were used to amplify a 433 bp long promoter. All the upstream primers (SEQ. ID. No 18 through No 23) were made to include a HindIII restriction enzyme region and the downstream primers (SEQ. ID. No 24) were made to include a XbaI restriction enzyme region (FIG. 2).

After digesting the PCR product with restriction enzymes HindIII/XbaI, DNA fragments were sub-cloned into pBI221 plasmid vector (Clontech, CaMV35S promoter, GUS coding region and NOS terminator were included) which was already digested with the same restriction enzymes. At last, deletion mutation plasmid vectors in various lengths, each having different deletion constructions of SWPA4 promoter (-2433, -1934, -1467, -1199, -818, and -433), were prepared and named 'p2433', 'p1934', 'p1467', 'p1199', 'p818' and 'p433'.

<3-2> Preparation of Deletion Mutants of the Promoter Less than 433 bp

In order to prepare deletion mutants having a promoter less than 433 bp, -433 bp long DNA fragment was amplified by PCR using ExTaq polymerase (Takara) and sequence specific primers, resulting in deletion promoter fragments in each 433, 366, 306, 177 and 110 bp length. At that time, primers represented by SEQ. ID. No 25 and No 24 were used to amplify a 366 bp long promoter, primers represented by SEQ. ID. No 26 and No 24 were used to amplify a 177 bp long promoter, and primers represented by SEQ. ID. No 28 and No 24 were used to amplify a 110 bp long promoter. All the upstream primers (SEQ. ID. No 25 through No 28) were designed to have a PstI restriction enzyme region.

Example 4

Investigation of a SWPA4 Promoter Activity Using Tobacco Protoplasts Transient Assay By taking advantage of deletion mutants of SWPA4 promoter, the promoter activity, according to the length of the deletion promoter, was investigated. First, a tobacco culture cell line BY-2 (Nicotiana tabacum L. cv. Bright yellow 2) was sub-cultured. Three days after the culture began, the cells were centrifuged to obtain cell membranes only, which were then treated with enzyme solution (30 ml; 1% cellulase R-10, 0.25% marcerozyme R-10, 60 mg MES, 30 mg BSA, 400 mM mannitol, 1 mM $CaCl_2$, distilled water 28 ml) for 3 hours. Protoplasts were separated by centrifugation. The separated protoplasts were washed twice with W5 solution (154 mM NaCl, 125 mM $CaCl_2$, 5 mM KCl, 5 mM glucose, 1.5 mM MES-KOH, pH 5.0), and final cell concentration was adjusted to $2\times10^6$ cells/ml in MaMg solution (0.4 M mannitol, 0.1% MES, 15 mM $MgCl_2$, pH 5.6). 5 µg of luciferase expression vector (Luc coding region was inserted in pBI221 for an internal control, Clontech), 300 µl of protoplast solution and 300 µl of PEG solution (40% PEG 3350, 100 mM $Ca(NO_3)_2$, 400 mM mannitol) were all mixed with 10 µg of each deletion mutant plasmid vector DNA prepared in the <Example 4>, which were leet at room temperature for 30 minuets. The mixture was washed with W5 solution by centrifugation, and suspended in 300 µl of W5 solution, followed by further culture at 25° C. for 16 hours. Upon completing the culture, cells were collected to investigate the activities of luciferase and GUS. In particular, the activity of luciferase was investigated by using luciferase assay kit supplied by Promega, and the activity of GUS promoter in protoplasts where a deletion mutant plasmid vector was inserted was investigated by measuring the amount of produced GUS protein according to the method of Jefferson et al. examining fluorescence by using MUG as a substrate (Jefferson et al., Plant Mol. Biol., 5, 387-405, 1987). The plasmid insertion efficiency into protoplast was also investigated by measuring the activity of luciferase inserted thereto at the same time.

Figure 3A:
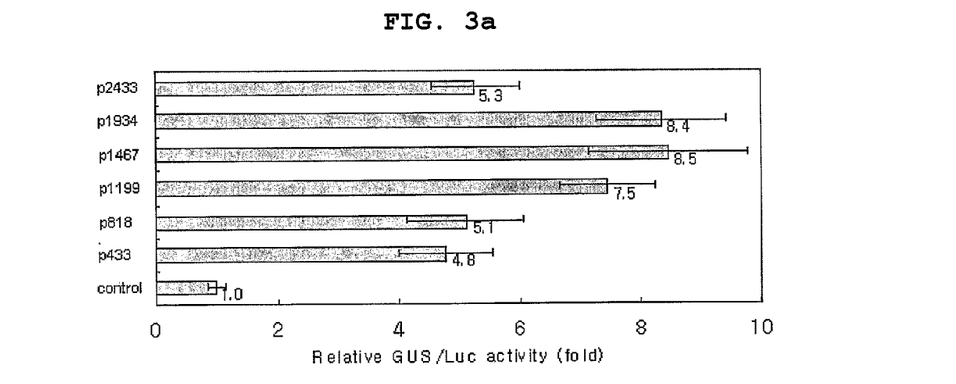
FIG. 3a is a graph showing the results of an investigation of a promoter activity using deletion mutants deficient in different promoter regions (p2433, p1934, p1467, p1199, p818, p433).
Figure 3B:
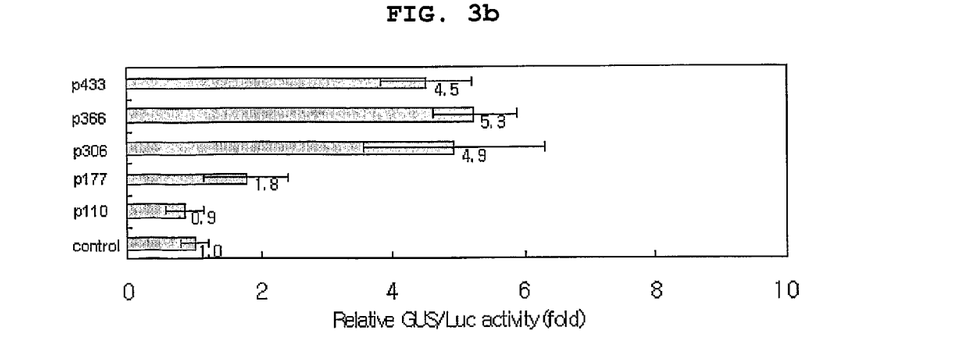
FIG. 3b is a graph showing the results of an investigation of a promoter activity using deletion mutants deficient in different promoter regions (p433, p366, p306, p177, p110). The promoter activity of CsMV 35S was measured as a control in FIG. 3a and FIG. 3b.

As a result, -2433 SWPA4 promoter showed about 5.3 fold higher activity than CaMV35S promoter. -1934 and -1467 promoters showed about 8.5 times higher activities and -1199 promoter showed about 7.5 times, -818 promoter showed about 5.1 times, and -433 promoter showed 4.8 times higher activity than a control (FIG. 3a). Based on that result, it was assumed that a transcription factor binding region suppressing expression was located between -2433 and -1934, and a transcription factor binding region promoting expression was located between -1467 showing the highest activity and -818 which was a turning point that the activity turned to decrease. -433 promoter having higher activity than CaMV35S promoter was re-made to be a shorter deletion structure, whose activity was then investigated. As a result, the activity of the shorter deletion mutant decreased and reached similar level to that of CaMV35S promoter at -177. Therefore, a minimum promoter length that can keep higher SWPA4 activity than CaMV35S was 301 bp and a binding region of a transcription regulation factor inducing a strong SWPA4 activity was believed to be located between -306 and -177 (FIG. 3b).

Example 5

Analysis on the Expression of GUS Gene in a Transgenic Plant by Using STPA4 Promoter <5-1> Preparation of a Transgenic Plant A tobacco plant (*Nicotiana tabacum* cv. *Xanthi*) was used as a material for the preparation of a transgenic plant. Only the promoter regions of plasmid vectors p2433, p1467 and p433 including SWPA4 promoter deletion mutant were digested with HindIII and XbaI, which were inserted in pBI121 (Clontech), which was obtained in advance by being digested with the same restriction enzymes, resulting in a plant expression vector. CaMV35S promoter was inserted for a control. Each vector prepared above was inserted in Agrobacteria by using *Agrobacterium tumefaciens* LBA4404 (ATCC), after which tobacco leaf fragments were infected with the same. The infected leaf fragments were cultured in MS medium containing 200 mg/l kanamycin and 300 mg/l claforan (Murashige T and Skoog F, *Physiol Plant*, 15, 473-497, 1962). Then, a transgenic plant was selected, which was acclimated by rooting and shooting. The plant was transplanted in a small flowerpot and became ready to be used as a test material.

In order to confirm if SWPA4 promoter deletion mutant was correctly inserted in a transgenic plant, PCR was performed with a pair of NPTII primer represented by SEQ. ID. No 29 and No 30 and a pair of primer for the amplification of 433 bp promoter represented by SEQ. ID. No 23 and No 24. When a pair of NPTII primer was used, PCR was performed at 95° C. for 1 minute, at 65° C. for 1 minute and at 72° C. for 1 minute (30 cycles). When a pair of primer for the amplification of 433 bp promoter was used, PCR was performed at 95° C. for 1 minute, at 62° C. for 1 minute and at 72° C. for 1 minute (30 cycles). Electrophoresis on agarose followed PCR to confirm PCR product.

As a result, 0.7 kb DNA fragment amplified by the pair of NPTII primer and 433 bp DNA fragment amplified by the pair of primer for the amplification of 433 bp promoter were detected in a transgenic plant. Thus, it was confirmed that a foreign gene was successfully inserted in the transgenic plant.

<5-2> Investigation of GUS Expression by Stress in a Transgenic Plant

In order to investigate the expression of SWPA4 promoter by an environmental stress in a transgenic plant, the transgenic plant was treated with methyl viologen (referred as 'MV' hereinafter) and pathogenic bacteria, and was wounded as well to measure the activity of GUS induced thereby.

At first, the expression of SWPA4 promoter by a wound was investigated. Particularly, a transgenic plant was wounded and then the activity of GUS induced thereby was measured. At that time, regarding GUS activity in a CaMV35S promoter plant as 100%, GUS activity in a SWPA4 promoter transgenic plant was represented by a relative activity. As a result, when a transgenic plant in which pBI121 vector containing CaMV35S promoter-GUS gene was inserted was treated with nothing (meaning 'control'), the GUS activity (pmol/minute/mg protein) was 7,200±135, which was hardly changed by stress like wound. In the case of transgenic plants each inserted with p2433, p1467 and p433 vector, the expression of GUS increased greatly three days after wounding. The expression of GUS in a transgenic plant infected with p1467 vector was 2.5 fold higher by a wound than that in CaMV35 promoter. The expression of GUS by a wound in a transgenic plant infected with p2433 vector could not compete with that in CaMV35S promoter, but the expression of GUS in a transgenic plant infected with p433 was as much as that in CaMV 35S promoter (Table 1). Therefore, it was confirmed that a promoter activity could be induced by wounding.

The expression of SWPA4 promoter by MV was also investigated. Particularly, leaf disks which were 7 mm in diameter were taken from a mature leaf. 20 disks were floated on each petridish containing 3 μM MV solution, which was cultured at 25° C. for 12 hours under darkness and then cultured under the light again. Upon completing the culture, GUS activity was measured to investigate the expression of SWPA4 promoter by MV. As a result, the expression of the promoter was strongly induced in SWPA4 deletion promoter plants 12 hours after the light-culture. The expression of GUS in a transgenic plant infected with p1467 vector was 2.5 fold higher than that in CaMV 35S promoter. And also, the expressions of GUS in transgenic plants infected with p2433 and p433 were each 1.8 fold and 2.1 fold increased, comparing to that in CaMV 35S promoter (Table 1).

In addition, a transgenic tobacco plant, in which a deletion mutant of peroxidase genomic gene SWPA4 promoter was inserted, was infected with a pathogenic bacterium (*Pseudomonas syringae* cv. *Tabaci*) causing wild fire disease in tobacco plants. 48 hours later, the activity of induced GUS was measured. As a result, the expressions of GUS in transgenic plants infected with p2433, p1467 and p433, respectively, were 2.2 fold, 2.7 fold and 2.0 fold increased each, comparing to that in CaMV 35S promoter (Table 1). Thus, the activities of GUS in all the three transgenic plant cases were greatly increased, comparing to that in control.

TABLE 1

Changes of GUS activity in transgenic tobacco plants by wounding, treating methyl viologen (MV) and treating a pathogenic bacterium (*Pseudomonas syringae* cv. tabaci)

| Expression vector | CaMV 35S | p2433 | p1467 | p433 |
|---|---|---|---|---|
| Control | 100% | 8 ± 2 | 12 ± 3 | 6 ± 1 |
| Wounding | 100% | 65 ± 5 | 250 ± 10 | 102 ± 8 |
| MV | 100% | 180 ± 11 | 315 ± 22 | 210 ± 11 |
| P. syringae | 100% | 220 ± 19 | 270 ± 20 | 200 ± 15 |

Taking all the above results into consideration, the activity of SWPA4 promoter was confirmed to be highly induced by non-biological or biological stresses. Thus, SWPA4 promoter of the present invention could be effectively used for the development of industrial multiple stress-resistant transgenic plants.

Example 6

Investigation of GUS Expression in Transgenic Plant Cells by Using SWPA4 Promoter <6-1> Preparation of Transgenic Culture Cells In order to produce transgenic culture cells, leaves of a transgenic tobacco plant in which a foreign gene was inserted were cultured in a callus-inducing medium prepared by adding 0.1 mg/l BAP, 2 mg/l NAA and 30 g/l sucrose to MS basal medium and callus was induced thereon by a conventional procedure. Particularly, calli were induced using transgenic tobacco leaves each infected with transforming vectors p2433, p1934, p1467, p1199, p818, p433, p366, p306, p177 and p110. Among those calli, the one that was infected with p1467 (-1467 deletion promoter) vector showed the highest promoter activity, which was named 'p1467 (*Nicotiana tabacum* cv. *Xanthi*) cell line' and deposited at Korean Collection for Type Culture (KCTC) of Korea Research Institute of Bioscience and Biotechnology (KRIBB) on Feb. 10, 2004 (Accession No: KCTC 10594BP).

<6-2> Investigation of a Promoter Activity in Transgenic Calli

In order to investigate how the expression of SWPA4 promoter of the present invention could affect or regulate culture cell proliferation, GUS activities in transgenic calli induced in transgenic plants infected with p2433, p1467, p433 and pBI121, respectively were measured. The measurement of GUS activity was performed following the same procedure above.

As a result, GUS activity (pmol/minute/mg protein) of plant culture cells containing SWPA4 promoter was 12,000±250, which was a percentage (%) to GUS activity of culture cells containing CaMV 35S promoter. All the GUS activities were higher in transgenic calli than in cells having CaMV 35S promoter, and especially, the callus infected with p1467 showed about 4.7 fold higher activity than that having CaMV 35S promoter. Calli, each infected with p2433 and p433, showed 3.1 fold and 2.5 fold higher activity respectively than a control (Table 2). Therefore, SWPA4 promoter was proved to be effectively used for the development of an industrial transgenic culture cell line available for producing a high-value protein.

TABLE 2

GUS activity of transgenic tobacco culture cells (calli)

| Expression vector | CaMV 35S | p2433 | p1467 | p433 |
|---|---|---|---|---|
| GUS activity | 100% | 310 ± 15% | 470 ± 25% | 250 ± 10% |

INDUSTRIAL APPLICABILITY

As explained hereinbefore, a promoter of peroxidase genomic gene SWPA4 includes many regions especially recognizing lots of environmental stresses and has at least 8-fold higher promoter activity than CaMV 35S promoter which has been widely used to induce an expression of a target gene in a transgenic plant. Therefore, the use of a plant or plant culture cells, in which the promoter of the present invention is inserted, facilitates the development of an environmental stress-resistant plant and the development of a transgenic organism mass-producing valuable substances.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated DNA sequence having multiple stress-inducible promoter activity, which comprises a base sequence selected from the group consisting of base sequences represented by SEQ ID NOS:2-11.

2. The DNA sequence according to claim 1, wherein the DNA sequence comprises a base sequence represented by nucleotides 2324 to 2433 of SEQ ID NO:11.

3. An expression vector for mass-production of a multiple stress-resistant substance, wherein a promoter sequence selected from the group consisting of base sequences represented by SEQ ID NOS:2-11, a coding sequence for the multiple stress-resistance substance and a terminator sequence are included in that order.

4. Transgenic cells for mass-production of a multiple stress-resistant substance, which are prepared by transfecting host plant cells with the expression vector of claim 3 and allowing expression of the multiple stress-resistant substance.

5. The transgenic cells as set forth in claim 4, wherein the host plant cells are the cells of a plant selected from the group consisting of tobacco, rice, sweet potato, and ginseng.

6. The transgenic cells as set forth in claim 4, wherein the cells are prepared by transfecting tobacco cells with the expression vector containing a base sequence represented by SEQ ID NO:9.

7. A transgenic plant for mass-production of a multiple stress-resistant substance, which is prepared by transfecting a host plant with the expression vector of claim 3 using an *Agrobacterium*.

8. The transgenic plant as set forth in claim 7, wherein the stress is selected from the group consisting of wounding, methyl viologen, hydrogen peroxide, NaCl, methyljasmonate, abscisic acid, and pathogenic bacteria.

9. A method of preparing a transgenic plant for mass-production of a multiple stress-resistant substance comprising the following steps:
   (a) constructing an expression vector containing one of the promoter sequences selected from the group consisting of base sequences represented by SEQ ID NOS:2-11, the multiple stress-resistant substance coding sequence and a transcription terminator sequence; and
   (b) transfecting a host plant with the expression vector of the above step (a) using an *Agrobacterium*, and wherein said multiple stress-resistant substance is expressed under the control of one of the promoter sequences of (a) in the plant and results in the mass production of said multiple stress-resistant substance.

10. The transgenic cells as set forth in claim 5, wherein the cells are prepared by transfecting tobacco cells with the expression vector containing a base sequence represented by SEQ ID NO:9.

* * * * *

SEQUENCE LISTING

```
<160> NUMBER OF SEQ ID NOS: 30

<210> SEQ ID NO 1
<211> LENGTH: 1512
<212> TYPE: DNA
<213> ORGANISM: Ipomoea batatas

<400> SEQUENCE: 1
atggcttcct ttgtcactcg gctcagcctg gcccttagct tcatcgccct agccctagct       60
ggcttctcca tttaccagaa tacccataca gccatgaaag ggcagcttaa gctcacccca      120
aagtggctgc tagacaacac tctagagtcg tcagtggccg acgtgctctc actacgccta      180
ggcatctcct ccggcaagct ttccgacgaa gactgcatat tctccgccgt taaggaagtg      240
gtggacgccg ccattgatgc agaaacccgc atgggtgctt ccctcattcg cctcttcttc      300
catgactgct ttgttgatgt acgtacgcta attttgtacg atgatgtttt tttttttttt      360 ttttttttc ccactgcatt atattaggaa attaaacaga ttgaaatgtg tgttattaat      420
gtattatctg cagggttgtg acgcaggtct tctactaaac gatacaccta ctttcaccgg      480
agaacagacc gccggcggca ataataactc agtcagaggt tttgaggtga tacaacaagc      540
taaagagaat gtgataacca aatgtcccta catacaagta tcttgtgccg acatcttatc      600
cattgctgcc cgtgattctt tccagagagt aagtccattt atttctaaag gttgaaatta      660
ataagaacaa gaatccaaac aaataacaga cagtaaaaaa aaaagattta tgtggtttga      720
caatatgttg aaattgtttt tatatttaat gactagtatt tatgcattat atttatatgc      780
aactctaaac atgcagttta ctggagaaac gtacaccgtg actctgggaa gactcgatgc      840
```

-continued

```
aagaacggcg aaccttaccg gagctaacac ccaactcgtc ggaccaaacg aggaattggc     900
atcgcaagtc gagaaatttg cggcgaaagg gttctccgaa acggagctag tcgccttgtt     960
aggtgttcac acggttgggt tttcgagatg tccgctttta tgcgttccca ttttcatcaa    1020
tcccgcccgg gcctccacgc tgcaatgcaa ctgtccggtg agtcccgacg acaccgggct    1080
ggtgggcctg gaccccactc cgttgacgtg ggaccaaagt ttttactccg acgtggctaa    1140
cggacaaggg cttctgttct ccgacaacga gctgatgaat agcaacacca ccagcgccgc    1200
cgttaggagg tacagggacg agatggacgc ttttctcgcc gatttcgccg ccgccatggt    1260
gaagatgagc ctcctgccgc cgtccccgg agtggagctc gaaatccgag aggtttgcag    1320
cgaggtgaat gccaacacag ttgcatccat gtgaagttcg ttcccatcga catcaataac    1380
gtctgtgatt ctgtgaaagt tttactcgga ctgtgaagaa ttttcacttt ctgttgtttc    1440
tgaaataaaa aagattttt ttttatgtcc taacaaaact tgtattactg aataaaattt    1500
ataaatttgt ta                                                        1512

<210> SEQ ID NO 2
<211> LENGTH: 110
<212> TYPE: DNA
<213> ORGANISM: Ipomoea batatas
<220> FEATURE:
<221> NAME/KEY: promoter
<222> LOCATION: (1)..(110)
<223> OTHER INFORMATION: -110 deletion promoter

<400> SEQUENCE: 2 tttcccttc aagttctcta tttaaggaag cctgagaagc cattaatcct catcatcagc      60
tcgaccactc atttcttctt catacttcct ttgctgtgat aatcatcatc                110

<210> SEQ ID NO 3
<211> LENGTH: 177
<212> TYPE: DNA
<213> ORGANISM: Ipomoea batatas
<220> FEATURE:
<221> NAME/KEY: promoter
<222> LOCATION: (1)..(177)
<223> OTHER INFORMATION: -177 deletion promoter

<400> SEQUENCE: 3
aaattaaatc tcagtttgct ttattatatt attatcaaca ataataattt aatactgatc      60
gaagaacttt cccttcaag ttctctattt aaggaagcct gagaagccat taatcctcat     120
catcagctcg accactcatt tcttcttcat acttcctttg ctgtgataat catcatc        177

<210> SEQ ID NO 4
<211> LENGTH: 306
<212> TYPE: DNA
<213> ORGANISM: Ipomoea batatas
<220> FEATURE:
<221> NAME/KEY: promoter
<222> LOCATION: (1)..(306)
<223> OTHER INFORMATION: -306 deletion promoter

<400> SEQUENCE: 4
taaggtgttt tatcgtggca gcatgagtgc atgacaaacg catatattat tattaaaaca      60
aaatagtact ccaatcataa taattatct tatattatat tgccaacaat taaaaattca     120
aattagaaca aattaaatct cagtttgctt tattatatta ttatcaacaa taataattta    180
atactgatcg aagaactttc cctttcaagt tctctattta aggaagcctg agaagccatt    240
```

-continued

```
aatcctcatc atcagctcga ccactcattt cttcttcata cttcctttgc tgtgataatc    300
atcatc                                                              306
```

<210> SEQ ID NO 5
<211> LENGTH: 366
<212> TYPE: DNA
<213> ORGANISM: Ipomoea batatas
<220> FEATURE:
<221> NAME/KEY: promoter
<222> LOCATION: (1)..(366)
<223> OTHER INFORMATION: -366 deletion promoter

<400> SEQUENCE: 5

```
tagtataatg aaataaagtt aatcattctc tatatttgat gatggtaatt agtatcatgg     60
taaggtgttt tatcgtggca gcatgagtgc atgacaaacg catatattat tattaaaaca    120
aaatagtact ccaatcataa taaattatct tatattatat tgccaacaat taaaaattca    180
aattagaaca aattaaatct cagtttgctt tattatatta ttatcaacaa taataattta    240
atactgatcg aagaactttc cctttcaagt tctctattta aggaagcctg agaagccatt    300
aatcctcatc atcagctcga ccactcattt cttcttcata cttcctttgc tgtgataatc    360
atcatc                                                              366
```

<210> SEQ ID NO 6
<211> LENGTH: 433
<212> TYPE: DNA
<213> ORGANISM: Ipomoea batatas
<220> FEATURE:
<221> NAME/KEY: promoter
<222> LOCATION: (1)..(433)
<223> OTHER INFORMATION: -433 deletion promoter

<400> SEQUENCE: 6

```
atggtgactt aaagggctga atccaacata tattctgaca tttaaaaatg ctaacgtacg     60
gttagattag tataatgaaa taaagttaat cattctctat atttgatgat ggtaattagt    120
atcatggtaa ggtgttttat cgtggcagca tgagtgcatg acaaacgcat atattattat    180
taaaacaaaa tagtactcca atcataataa attatcttat attatattgc caacaattaa    240
aaattcaaat tagaacaaat taaatctcag tttgctttat tatattatta tcaacaataa    300
taatttaata ctgatcgaag aactttccct ttcaagttct ctatttaagg aagcctgaga    360
agccattaat cctcatcatc agctcgacca ctcatttctt cttcatactt cctttgctgt    420
gataatcatc atc                                                      433
```

<210> SEQ ID NO 7
<211> LENGTH: 818
<212> TYPE: DNA
<213> ORGANISM: Ipomoea batatas
<220> FEATURE:
<221> NAME/KEY: promoter
<222> LOCATION: (1)..(818)
<223> OTHER INFORMATION: -818 deletion promoter

<400> SEQUENCE: 7

```
gcttcacgca ctcaactagt cacatctttc caggcaaaat ttacttttct atgaatatga     60
gaagttccat ctatggaaat aacggattat ttatctaatt ttcaaattct atatatatag    120
tctcgagtgg aacaaaaata gaactaattt gaacaaatca aagtctaaga aaataataca    180
tgctttagca gcaaaaataa gaatggtact atacttaatc ctcatcatag tcttcaaccc    240
tgcatatagc acacttaaca ttttatattc aaatatactt taatttagtc atgataatac    300
```

```
aactcaccta ctccattata gccgataata caactcacct agctactcca ttatagtcca    360
acaatatcaa atgaataaaa tagtaatggt gacttaaagg gctgaatcca acatatattc    420
tgacatttaa aaatgctaac gtacggttag attagtataa tgaaataaag ttaatcattc    480
tctatatttg atgatggtaa ttagtatcat ggtaaggtgt tttatcgtgg cagcatgagt    540
gcatgacaaa cgcatatatt attattaaaa caaaatagta ctccaatcat aataaattat    600
cttatattat attgccaaca attaaaaatt caaattagaa caaattaaat ctcagtttgc    660
tttattatat tattatcaac aataataatt taatactgat cgaagaactt cccctttcaa    720
gttctctatt taaggaagcc tgagaagcca ttaatcctca tcatcagctc gaccactcat    780
ttcttcttca tacttccttt gctgtgataa tcatcatc                            818

<210> SEQ ID NO 8
<211> LENGTH: 1199
<212> TYPE: DNA
<213> ORGANISM: Ipomoea batatas
<220> FEATURE:
<221> NAME/KEY: promoter
<222> LOCATION: (1)..(1199)
<223> OTHER INFORMATION: -1199 deletion promoter

<400> SEQUENCE: 8
atgcagggtg aaagtaagat tgaatatact gatactacaa ttaactaatg ataaagtata     60
acttttgtaa aaaatttgat ttttttttt gatgaattca tatactccaa agattttcct    120
catttaatta aatttctatc ctcatgttga acccattaat cgaataattg acatattaga    180
taaacttagc catcatatga catttgatca tgattgatga ttttttaaaa ataaaaacaa    240
aattatgaaa gggtaatgaa atattttaaa aaaattatgt aaaccctgta atctagtaat    300
ctgtacaata ataattttgt ttcaactaag aggatgttgg caaaagtata attaaacttg    360
tgatcttcgt acaataatta tgcttcacgc actcaactag tcacatcttt ccaggcaaaa    420 tttactttc tatgaatatg agaagttcca tctatggaaa taacggatta tttatctaat    480
tttcaaattc tatatatata gtctcgagtg gaacaaaaat agaactaatt tgaacaaatc    540
aaagtctaag aaaataatac atgctttagc agcaaaaata agaatggtac tatacttaat    600
cctcatcata gtcttcaacc ctgcatatag cacacttaac atttatatt caaatatact    660 ttaatttagt catgataata caactcacct actccattat agccgataat acaactcacc    720
tagctactcc attatagtcc aacaatatca aatgaataaa atagtaatgg tgacttaaag    780
ggctgaatcc aacatatatt ctgacattta aaaatgctaa cgtacggtta gattagtata    840
atgaaataaa gttaatcatt ctctatattt gatgatggta attagtatca tggtaaggtg    900
ttttatcgtg gcagcatgag tgcatgacaa acgcatatat tattattaaa acaaaatagt    960
actccaatca taataaatta tcttatatta tattgccaac aattaaaaat tcaaattaga   1020
acaaattaaa tctcagtttg ctttattata ttattatcaa caataataat ttaatactga   1080
tcgaagaact tcccctttca agttctctat ttaaggaagc tgagaagcc attaatcctc   1140 atcatcagct cgaccactca tttcttcttc atacttcctt tgctgtgata atcatcatc   1199

<210> SEQ ID NO 9
<211> LENGTH: 1467
<212> TYPE: DNA
<213> ORGANISM: Ipomoea batatas
<220> FEATURE:
<221> NAME/KEY: promoter
<222> LOCATION: (1)..(1467)
```

<223> OTHER INFORMATION: -1467 deletion promoter

<400> SEQUENCE: 9

| | |
|---|---|
| ggctgtccgg aattctgtct ctctggacca gttttggcaa acaatttga aaccacactt | 60 |
| atactactcc aaaaattatg aaattttat ggtagcttct acacttatag aactacatgt | 120 |
| ataaaaata ttgggtcaaa ataccttacc gattttccc aaatattcac ggaacttact | 180 |
| gccagaatct accctgcttt ttcctttcac tattttcaca actataagca tatatgggca | 240 |
| taaatatgac atgaacatgc atgaaccaat gcagggtgaa agtaagattg aatatactga | 300 |
| tactacaatt aactaatgat aaagtataac ttttgtaaaa aatttgattt tttttttga | 360 |
| tgaattcata tactccaaag attttcctca tttaattaaa tttctatcct catgttgaac | 420 |
| ccattaatcg aataattgac atattagata aacttagcca tcatatgaca tttgatcatg | 480 |
| attgatgatt tttaaaaaat aaaaacaaaa ttatgaaagg gtaatgaaat attttaaaaa | 540 |
| aattatgtaa accctgtaat ctagtaatct gtacaataat aattttgttt caactaagag | 600 |
| gatgttggca aaagtataat taaacttgtg atcttcgtac aataattatg cttcacgcac | 660 |
| tcaactagtc acatctttcc aggcaaaatt tactttcta tgaatatgag aagttccatc | 720 |
| tatggaaata acggattatt tatctaattt tcaaattcta tatatatagt ctcgagtgga | 780 |
| acaaaaatag aactaatttg aacaaatcaa agtctaagaa aataatacat gctttagcag | 840 |
| caaaaataag aatggtacta tacttaatcc tcatcatagt cttcaaccct gcatatagca | 900 |
| cacttaacat tttatattca aatatacttt aatttagtca tgataataca actcacctac | 960 |
| tccattatag ccgataatac aactcaccta gctactccat tatagtccaa caatatcaaa | 1020 |
| tgaataaaat agtaatggtg acttaaaggg ctgaatccaa catatattct gacatttaaa | 1080 |
| aatgctaacg tacggttaga ttagtataat gaaataaagt taatcattct ctatatttga | 1140 |
| tgatggtaat tagtatcatg gtaaggtgtt ttatcgtggc agcatgagtg catgacaaac | 1200 |
| gcatatatta ttattaaaac aaaatagtac tccaatcata ataaattatc ttatattata | 1260 |
| ttgccaacaa ttaaaaattc aaattagaac aaattaaatc tcagtttgct ttattatatt | 1320 |
| attatcaaca ataataattt aatactgatc gaagaacttt cccttcaag ttctctattt | 1380 |
| aaggaagcct gagaagccat taatcctcat catcagctcg accactcatt tcttcttcat | 1440 |
| acttcctttg ctgtgataat catcatc | 1467 |

<210> SEQ ID NO 10
<211> LENGTH: 1934
<212> TYPE: DNA
<213> ORGANISM: Ipomoea batatas
<220> FEATURE:
<221> NAME/KEY: promoter
<222> LOCATION: (1)..(1934)
<223> OTHER INFORMATION: -1934 deletion promoter

<400> SEQUENCE: 10

| | |
|---|---|
| ttgccatctc accacttcgt cttaaacaat ctaggatatt cttagatatt cttcatactc | 60 |
| aagtctcaca cttgaaatca atcaagactc ttacactaac aattcctcaa tatacctcat | 120 |
| aatatcatct ctacttaaac tagagagatt ccaactctc aattaatcac caaaggtaac | 180 |
| tctccaaata tccaaatgga aggtttcaac ttccaaacta ataccaaacc aaccggacta | 240 |
| atcataatca tattcataat cataaattgt ttctaactgc ccctgtccag aaattacagt | 300 |
| tttgcgcagt ccgaaagatt gagccggtaa caatagttcc cgaactcttt ttcacttgaa | 360 |
| attttatgg tagaacccta acttatagta cttgatatcc ataaaagtt ttggtcacct | 420 |

```
aggttcacga attaacacag aaaattacat ctttgccctt ggcagtgggc tgtccggaat      480
tctgtctctc tggaccagtt ttggcaaaca attttgaaac cacacttata ctactccaaa     540
aattatgaaa ttttatggt agcttctaca cttatagaac tacatgtata aaaatattg       600 ggtcaaaata ccttaccgat ttttcccaaa tattcacgga acttactgcc agaatctacc     660 ctgcttttc ctttcactat tttcacaact ataagcatat atgggcataa atatgacatg      720
aacatgcatg aaccaatgca gggtgaaagt aagattgaat atactgatac tacaattaac    780
taatgataaa gtaaacttt tgtaaaaaat ttgatttttt tttttgatga attcatatac      840
tccaaagatt ttcctcattt aattaaattt ctatcctcat gttgaaccca ttaatcgaat     900
aattgacata ttagataaac ttagccatca tatgacattt gatcatgatt gatgattttt    960
aaaaaataaa aacaaaatta tgaaagggta atgaaatatt ttaaaaaaat tatgtaaacc    1020
ctgtaatcta gtaatctgta caataataat tttgtttcaa ctaagaggat gttggcaaaa    1080
gtataattaa acttgtgatc ttcgtacaat aattatgctt cacgcactca actagtcaca    1140
tctttccagg caaaattac ttttctatga atatgagaag ttccatctat ggaaataacg     1200
gattatttat ctaattttca aattctatat atatagtctc gagtggaaca aaaatagaac    1260
taatttgaac aaatcaaagt ctaagaaaat aatacatgct ttagcagcaa aaataagaat    1320
ggtactatac ttaatcctca tcatagtctt caaccctgca tatagcacac ttaacattt     1380 atattcaaat atactttaat ttagtcatga taatacaact cacctactcc attatagccg    1440
ataatacaac tcacctagct actccattat agtccaacaa tatcaaatga ataaaatagt    1500
aatggtgact taagggctg aatccaacat atattctgac atttaaaaat gctaacgtac     1560
ggttagatta gtataatgaa ataaagttaa tcattctcta tatttgatga tggtaattag    1620
tatcatggta aggtgtttta tcgtggcagc atgagtgcat gacaaacgca tatattatta    1680
ttaaaacaaa aatagtactcc aatcataata aattatctta tattatattg ccaacaatta   1740
aaaattcaaa ttagaacaaa ttaaatctca gtttgcttta ttatattat atcaacaata    1800 ataaatttaat actgatcgaa gaactttccc tttcaagttc tctatttaag gaagcctgag   1860
aagccattaa tcctcatcat cagctcgacc actcattct tcttcatact tcctttgctg     1920
tgataatcat catc                                                      1934
```

<210> SEQ ID NO 11
<211> LENGTH: 2433
<212> TYPE: DNA
<213> ORGANISM: Ipomoea batatas
<220> FEATURE:
<221> NAME/KEY: promoter
<222> LOCATION: (1)..(2433)
<223> OTHER INFORMATION: -2433 promoter

<400> SEQUENCE: 11

```
cctcatggag tattctcata actctcttca gtatgaatga atcatacaat acaacgcagc      60
gacgaataga cttcgccctg aactagacat acgacaacat agccaccata cgggaaaggc    120
acttcaagct ctttatcccg taggctgcaa caacataacg acataacgac cactgggcaa    180 ggcatttac agccacccgt gggtcaatca aggtcctcct cactcacttt agaaactaag     240
ggtttgaaaa catgatcttt ccttcagttt ttcttacaac aaatcattca ctttggacac    300
atttcacaat tgagtccaat acttaaaccg gctacttcat tagcccctga aggattttaa    360
aaaaaacttt cactgcccgc aggctcttca aacatctttt cctcattatc aagtgaggca    420
```

-continued

```
ttttcctcaa aagtaaggtt ttgacaacct ttatatcaaa atagcatacg tttttcaacg    480
taagtttcat aacatttact tgccatctca ccacttcgtc ttaaacaatc taggatattc    540
ttagatattc ttcatactca agtctcacac ttgaaatcaa tcaagactct tacactaaca    600
attcctcaat atacctcata atatcatctc tacttaaact agagagattt ccaactctca    660
attaatcacc aaaggtaact ctccaaatat ccaaatggaa ggtttcaact tccaaactaa    720
taccaaacca accggactaa tcataatcat attcataatc ataaattgtt tctaactgcc    780
cctgtccaga aattacagtt ttgcgcagtc cgaaagattg agccggtaac aatagttccc    840
gaactctttt tcacttgaaa tttttatggt agaaccctaa cttatagtac ttgatatcca    900 taaaagttt tggtcaccta ggttcacgaa ttaacacaga aaattacatc tttgcccttg    960
gcagtgggct gtccggaatt ctgtctctct ggaccagttg tggcaaacaa ttttgaaacc   1020
acacttatac tactccaaaa attatgaaat ttttatggta gcttctacac ttatagaact   1080
acatgtataa aaaatattgg gtcaaaatac cttaccgatt tttcccaaat attcacggaa   1140
cttactgcca gaatctaccc tgcttttttcc tttcactatt ttcacaacta taagcatata   1200
tgggcataaa tatgacatga acatgcatga accaatgcag ggtgaaagta agattgaata   1260
tactgatact acaattaact aatgataaag tataacttttt gtaaaaaatt tgatttttttt  1320 ttttgatgaa ttcatatact ccaaagattt tcctcattta attaaatttc tatcctcatg   1380
ttgaacccat taatcgaata attgacatat tagataaact tagccatcat atgacatttg   1440
atcatgattg atgatttttta aaaataaaa acaaaattat gaaagggtaa tgaaatattt   1500
taaaaaaatt atgtaaaccc tgtaatctag taatctgtac aataataatt ttgtttcaac   1560
taagaggatg ttggcaaaag tataattaaa cttgtgatct tcgtacaata attatgcttc   1620
acgcactcaa ctagtcacat ctttccaggc aaaatttact tttctatgaa tatgagaagt   1680
tccatctatg gaaataacgg attatttatc taattttcaa attctatata tatagtctcg   1740
agtggaacaa aaatagaact aatttgaaca aatcaaagtc taagaaaata atacatgctt   1800
tagcagcaaa aataagaatg gtactatact taatcctcat catagtcttc aaccctgcat   1860
atagcacact taacattttta tattcaaata tactttaatt tagtcatgat aatacaactc   1920
acctactcca ttatagccga taatacaact cacctagcta ctccattata gtccaacaat   1980
atcaaatgaa taaatagta atggtgactt aaagggctga atccaacata tattctgaca   2040
tttaaaaatg ctaacgtacg gttagattag tataatgaaa taaagttaat cattctctat   2100
atttgatgat ggtaattagt atcatggtaa ggtgttttat cgtggcagca tgagtgcatg   2160
acaaacgcat atattattat taaaacaaaa tagtactcca atcataataa attatcttat   2220
attatattgc caacaattaa aaattcaaat tagaacaaat taaatctcag tttgcttttat  2280 tatattatta tcaacaataa taatttaata ctgatcgaag aactttccct ttcaagttct   2340
ctatttaagg aagcctgaga agccattaat cctcatcatc agctcgacca ctcatttctt   2400
cttcatactt cctttgctgt gataatcatc atc                               2433
```

<210> SEQ ID NO 12
<211> LENGTH: 26
<212> TYPE: DNA
<213> ORGANISM: Artificial Sequence
<220> FEATURE:
<223> OTHER INFORMATION: GSP1 promoter

<400> SEQUENCE: 12
ctgagccgag tgacaaagga agccat    26

```
<210> SEQ ID NO 13
<211> LENGTH: 22
<212> TYPE: DNA
<213> ORGANISM: Artificial Sequence
<220> FEATURE:
<223> OTHER INFORMATION: AP1 promoter

<400> SEQUENCE: 13
gtaatacgac tcactatagg gc                                              22

<210> SEQ ID NO 14
<211> LENGTH: 25
<212> TYPE: DNA
<213> ORGANISM: Artificial Sequence
<220> FEATURE:
<223> OTHER INFORMATION: GSP2 promoter

<400> SEQUENCE: 14
cacagcaaag gaagtatgaa gaagc                                           25

<210> SEQ ID NO 15
<211> LENGTH: 19
<212> TYPE: DNA
<213> ORGANISM: Artificial Sequence
<220> FEATURE:
<223> OTHER INFORMATION: AP2 promoter

<400> SEQUENCE: 15
actatagggc acgcgtggt                                                  19

<210> SEQ ID NO 16
<211> LENGTH: 26
<212> TYPE: DNA
<213> ORGANISM: Artificial Sequence
<220> FEATURE:
<223> OTHER INFORMATION: exon promoter

<400> SEQUENCE: 16
atggcttcct ttgtcactcg gctcag                                          26

<210> SEQ ID NO 17
<211> LENGTH: 30
<212> TYPE: DNA
<213> ORGANISM: Artificial Sequence
<220> FEATURE:
<223> OTHER INFORMATION: intron promoter

<400> SEQUENCE: 17
tcatcagctc gaccactcat ttcttcttca                                      30

<210> SEQ ID NO 18
<211> LENGTH: 35
<212> TYPE: DNA
<213> ORGANISM: Artificial Sequence
<220> FEATURE:
<223> OTHER INFORMATION: forward promoter for -2433 deletion promoter

<400> SEQUENCE: 18
gccaagcttg gtcctcatgg agtattctca taact                                35

<210> SEQ ID NO 19
<211> LENGTH: 33
<212> TYPE: DNA
<213> ORGANISM: Artificial Sequence
<220> FEATURE:
```

<223> OTHER INFORMATION: forward primer for -1934 deletion promoter

<400> SEQUENCE: 19
gccaagcttt tgccatctca ccacttcgtc tta                33

<210> SEQ ID NO 20
<211> LENGTH: 31
<212> TYPE: DNA
<213> ORGANISM: Artificial Sequence
<220> FEATURE:
<223> OTHER INFORMATION: forward primer for -1467 deletion promoter

<400> SEQUENCE: 20
gccaagcttg gctgtccgga attctgtctc t                31

<210> SEQ ID NO 21
<211> LENGTH: 33
<212> TYPE: DNA
<213> ORGANISM: Artificial Sequence
<220> FEATURE:
<223> OTHER INFORMATION: forward primer for -1199 deletion promoter

<400> SEQUENCE: 21
gccaagctta tgcagggtga aagtaagatt gaa                33

<210> SEQ ID NO 22
<211> LENGTH: 26
<212> TYPE: DNA
<213> ORGANISM: Artificial Sequence
<220> FEATURE:
<223> OTHER INFORMATION: forward primer for -818 deletion promoter

<400> SEQUENCE: 22
gccaagcttg cttcacgcac tcaact                26

<210> SEQ ID NO 23
<211> LENGTH: 33
<212> TYPE: DNA
<213> ORGANISM: Artificial Sequence
<220> FEATURE:
<223> OTHER INFORMATION: forward primer for -433 deletion promoter

<400> SEQUENCE: 23
gccaagctta tggtgactta aagggctgaa tcc                33

<210> SEQ ID NO 24
<211> LENGTH: 34
<212> TYPE: DNA
<213> ORGANISM: Artificial Sequence
<220> FEATURE:
<223> OTHER INFORMATION: reverse primer for -2433, 1934, 1467, 1199,
       818, 433, 366, 306, 177 and 110 deletion promoter

<400> SEQUENCE: 24
tcctctagag atgatgatta tcacagcaaa ggaa                34

<210> SEQ ID NO 25
<211> LENGTH: 31
<212> TYPE: DNA
<213> ORGANISM: Artificial Sequence
<220> FEATURE:
<223> OTHER INFORMATION: forward primer for -366 deletion promoter

<400> SEQUENCE: 25
ttcctgcaga tagtataatg aaataaagtt a                31

```
<210> SEQ ID NO 26
<211> LENGTH: 26
<212> TYPE: DNA
<213> ORGANISM: Artificial Sequence
<220> FEATURE:
<223> OTHER INFORMATION: forward primer for -306 deletion promoter

<400> SEQUENCE: 26
tttctgcagt aaggtgtttt atcgtg                                          26

<210> SEQ ID NO 27
<211> LENGTH: 25
<212> TYPE: DNA
<213> ORGANISM: Artificial Sequence
<220> FEATURE:
<223> OTHER INFORMATION: forward primer for -177 deletion promoter

<400> SEQUENCE: 27
ttcctgcaga aattaaatct cagtt                                           25

<210> SEQ ID NO 28
<211> LENGTH: 24
<212> TYPE: DNA
<213> ORGANISM: Artificial Sequence
<220> FEATURE:
<223> OTHER INFORMATION: forward primer for -110 deletion promoter

<400> SEQUENCE: 28
ttcctgcagt ttccctttca agtt                                            24

<210> SEQ ID NO 29
<211> LENGTH: 19
<212> TYPE: DNA
<213> ORGANISM: Artificial Sequence
<220> FEATURE:
<223> OTHER INFORMATION: forward primer for NPTII

<400> SEQUENCE: 29
gaggctattc ggctagatg                                                  19

<210> SEQ ID NO 30
<211> LENGTH: 21
<212> TYPE: DNA
<213> ORGANISM: Artificial Sequence
<220> FEATURE:
<223> OTHER INFORMATION: reverse primer for NPTII

<400> SEQUENCE: 30
atcgggagcg gcgataccgt a                                               21
```